US00PP23885P3

(12) United States Plant Patent
Pflum

(10) Patent No.: US PP23,885 P3
(45) Date of Patent: Sep. 10, 2013

(54) AVOCADO TREE NAMED 'PFLUM'S BEST'

(50) Latin Name: ***Persea americana* Mill**
Varietal Denomination: Pflum's Best

(76) Inventor: Julius Pflum, Palm City, FL (US)

( * ) Notice: Subject to any disclaimer, the term of this patent is extended or adjusted under 35 U.S.C. 154(b) by 76 days.

(21) Appl. No.: 13/374,409

(22) Filed: Dec. 27, 2011

(65) Prior Publication Data

US 2013/0167274 P1 Jun. 27, 2013

(51) Int. Cl.
*A01H 5/00* (2006.01)

(52) U.S. Cl.
USPC ..... Plt./200

(58) Field of Classification Search
USPC ..... Plt./200
See application file for complete search history.

(56) References Cited

U.S. PATENT DOCUMENTS

| | | | |
|---|---|---|---|
| PP12,439 | P2 | 3/2002 | Krome et al. |
| PP14,089 | P3 | 8/2003 | Llanos |
| PP14,238 | P3 | 10/2003 | Bergh et al. |
| PP14,239 | P3 | 10/2003 | Martin et al. |
| PP15,309 | P3 | 11/2004 | Kohne |
| PP16,594 | P3 | 5/2006 | Pimentel |
| PP17,947 | P3 | 8/2007 | Darvas |
| PP18,459 | P3 | 1/2008 | Brooks |
| PP21,099 | P3 | 6/2010 | Joubert |

*Primary Examiner* — Annette Para
(74) *Attorney, Agent, or Firm* — Christopher & Weisberg, P.A.

(57) ABSTRACT

A new avocado variety called 'Pflum's Best' that displays an early fruiting season, precocity, vigorous growth, tolerance to wet soil, and large maroon fruit. The variety is also selected for its resistance and tolerance to common avocado diseases and various insects. Additionally, 'Pflum's Best' bears fruit earlier, by one to three years, than its male parent 'Brogdon' and female parent 'Choquette.' The characteristic maroon skin of the fruit of 'Pflum's Best' has a subtle texture and may be somewhat mottled with a light green color, and the flesh has an exceptionally delicious taste that is buttery and nutty. The fruit of 'Pflum's Best' is approximately 6-11 inches in length, 4.5 inches in diameter, and approximately 25 ounces when ripe.

4 Drawing Sheets

Latin name: *Persea americana* Mill.
Variety denomination: 'Pflum's Best'.

BACKGROUND OF THE VARIETY

'Pflum's Best' is a new and distinct variety of avocado tree *Persea americana* Mill. During the 1980s, the inventor chose two varieties known for their commercial value, 'Choquette' (not patented) and 'Brogdon' (not patented), and cross-pollinated them to produce a first generation (F1) of hybrid avocado trees in Princeton, Fla. Some of the seedlings were selected because they exhibited faster growth and increased tolerance to dampness, poorly-drained soil, and cold temperatures. The selected seedlings were grown to maturity, at which time it was discovered that the selected variety, named 'Pflum's Best', produces large, maroon-skinned fruit very early in the season (in August to September). Further, the variety displays vigorous growth and is very precocious, producing fruit at one to five years when grown from seed.

The male parent, 'Brogdon,' is a Mexican or Mexican hybrid having a "B type' flowers and small, pear-shaped fruit with pebbled dark purple to black skin. The fruit has a superb buttery flavor and is commonly used for guacamole. In addition to having a high tolerance to cold (this variety is cold hardy to approximately 22° F.), good pest and disease resistance (although moderately susceptible to scab, *Sphaceloma perseae*), and excellent toleration of drought, heat, and humidity, 'Brogdon' exhibits a relatively early fruiting season (mid-July to mid-September). However, the crop consistency and quantity may be low and 'Brogdon' can be easily damaged by wet soil and the associated *Phytophthora* spp. (such as *P. cinnamomi*). The female parent, 'Choquette,' is a popular variety with both commercial growers and homeowners. 'Choquette' is a Guatemalan/West Indian hybrid having "A type" flowers and large, high quality, oval fruit with glossy, bright to dark green skin. Although 'Choquette' produces a high yield in alternate years and displays vigorous growth, it does not exhibit quite the cold and disease resistance of 'Brogdon' (freeze damage occurs below 26° F.) and fruits much later in the season (late October to mid-January).

The inventor first cross-pollinated 'Brogdon' and 'Choquette' in 1989 in an effort to produce an avocado variety having the best qualities of each parent. F1 generation seedlings and young trees were selected for vigorous growth and disease hardiness, and then mature F1 adults were further selected for distinct fruit characteristics and early fruiting season. The resulting group, first defined in Princeton, Fla., in 1992, was named 'Pflum's Best.' This variety was first asexually propagated in 1990 in Palm City, Fla. using a lateral grafting technique and 'Walden' rootstock (not patented), and has since been observed to remain true to type over successive asexually propagated generations.

BRIEF DESCRIPTION OF THE VARIETY

'Pflum's Best' was selected for its early fruiting season, precocity, vigorous growth, tolerance to wet soil, and large maroon fruit. The variety was also selected for its resistance to common avocado diseases such as *Cercospora* spot (*Cercospora purpurea*), avocado scab (*Sphaceloma perseae*), avocado root rot (*Phytophthora cinnamomi*), powdery mildew (*Oidium* sp.), algal leaf spot (*Cephaleuros* sp.), *diplodia* stem-end rot (*Diplodia* sp.), and tolerance to common avocado diseases such as anthracnose (*Colletotrichum gloeosporoides*), sun-blotch, and various insects. Additionally, 'Pflum's Best' bears fruit earlier, by one to three years, than either of its parents. The characteristic maroon skin of the fruit of 'Pflum's Best' has a subtle texture and may be somewhat mottled with a light green color, and the flesh has an exceptionally delicious taste that is buttery and nutty. The fruit of 'Pflum's Best' is larger than both 'Brogdon' (which averages approximately 4 inches in length, 8-12 ounces) and 'Choquette' (which averages 6 inches in length, 18-40 ounces), having an average length of approximately 6-11 inches in length and 4.5 inches in diameter when ripe. Although 'Pflum's Best' does not possess all the desirable characteristics of both parents (e.g., good cold tolerance of 'Brogdon' and high yield of 'Choquette'), 'Pflum's Best' does display desirable traits that would benefit both commercial growers and homeowners.

BRIEF DESCRIPTION OF THE PHOTOGRAPHS

A more complete understanding of the present invention, and the attendant advantages and features thereof, will be more readily understood by reference to the following detailed description when considered in conjunction with the accompanying drawings wherein.

DETAILED BOTANICAL DESCRIPTION OF THE VARIETY

The following detailed botanical description is based on observations made during the 2011 growing season in Palm City, Fla. of two- to thirteen-year-old 'Pflum's Best' trees grown on 'Walden' rootstock. All colors are described according to the Pantone color system. It should be understood that the characteristics described will vary somewhat depending on cultural practices and climatic conditions, and will vary with location and season. Quantified measurements are expressed as an average of measurements taken from a number of individual plants of the new variety. The measurements of any individual plant or any group of plants of the new variety may vary from the stated average.

When observed as described, the variety was grown in light, well-drained soil having flat topography. The variety was being fertilized approximately twice per year with a 6-4-6 fertilizer.

Figure 1:
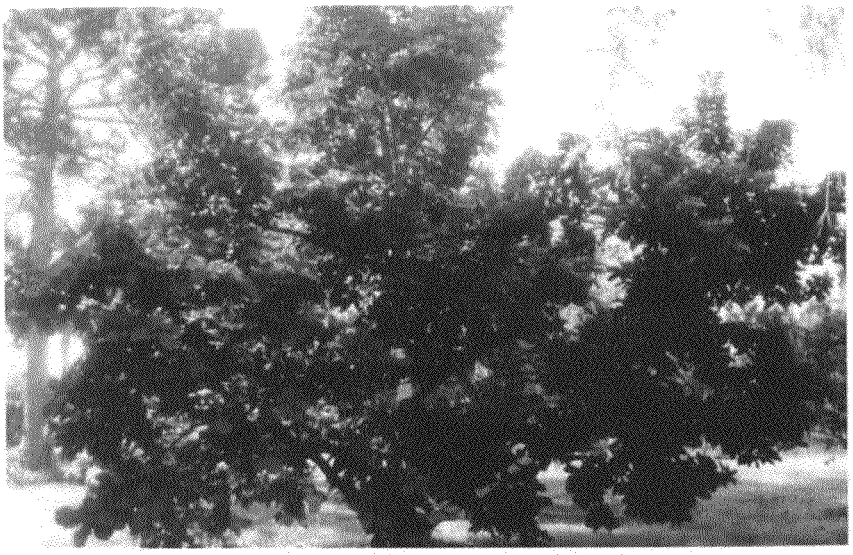
FIG. 1 shows an adult 'Pflum's Best' tree (approximately 13 years of age) displaying upright, asymmetrical growth habit and acute crotch angles.
Figure 2:
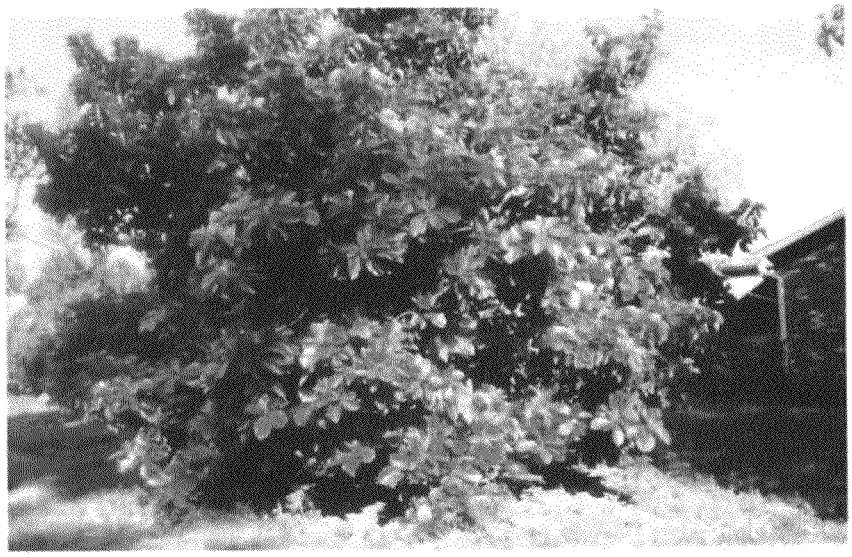
FIG. 2 shows an adult 'Pflum's Best' tree (approximately 12 years of age) displaying upright, asymmetrical growth habit with dense growth near the base of the tree.
Figure 3:
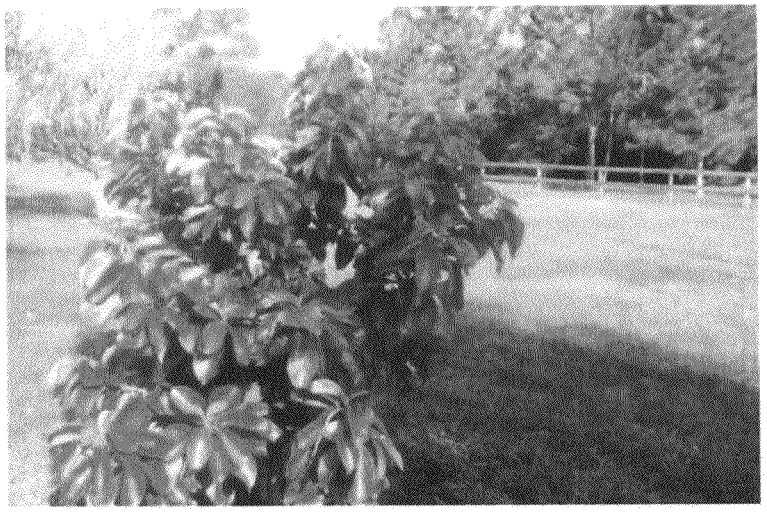
FIG. 3 shows a younger 'Pflum's Best' tree (approximately two years of age) displaying anthocyanin coloration and upright growth habit.

Tree (as seen in FIGS. 1-3):

*Height.*—Approximately 5.5 feet at 2 years of age; approximately 30 feet at 13 years of age.

*Spread.*—Approximately 19 feet at 13 years of age.

*Vigor.*—Very vigorous growth, substantially evergreen.

*Branching habit.*—At 12 years of age, tree is upright and asymmetrical with dense growth, especially near the base of the tree. As seen especially in FIG. 1, several upright branches split off the vertical trunk, these upright branches also being split into smaller branches.

*Production.*—Medium production (approximately 50 lbs per tree per year).

*Bearing.*—Matures (bears fruit) early, within one to five years; annual bearing.

*Trunk.*—Diameter is approximately 8⅔ inches at 13 years of age.

*Bark texture.*—Light grooves and ridges.

*Bark color.*—Light brown (approximately Pantone DS 318-7U).

*Trunk lenticels.*—Approximately 2 per square inch.

Branch (as seen in FIGS. 1-3):

*Average diameter of older branches.*—Approximately 5¼ inches at 12 years of age.

*Average diameter of younger branches.*—Approximately ⅜ inch at two months of age.

*Crotch angle.*—Acute (approximately less than 90 degrees, with average of approximately 60 degrees).

*Texture.*—Very light grooves and ridges.

*Color, most recent flush.*—Light greenish yellow (approximately Pantone DS 302-5U).

*Color, previous flush.*—Mild brown to brownish green (approximately Pantone DS 42-5 U to Pantone DS 313-5 U).

*Lenticels.*—Approximately 5 per square inch.

Figure 4:
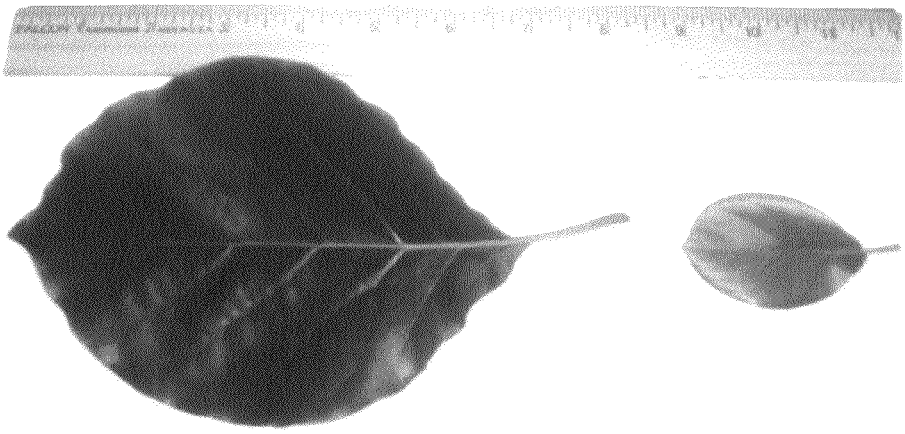
FIG. 4 shows the upper side of both a mature 'Pflum's Best' leaf (over one year of age) and younger leaf (approximately one month of age), displaying pinnate venation and described leaf shape.
Figure 5:
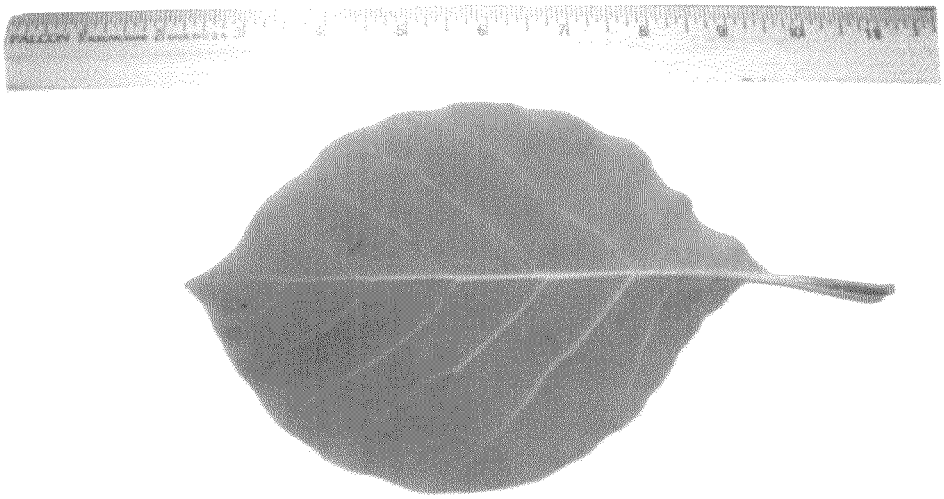
FIG. 5 shows the lower side of a mature 'Pflum's Best' leaf (over one year of age) displaying pinnate venation and described leaf shape.

Leaves (as seen in FIGS. 4-5):

*Length.*—Mature leaves (older than one year of age) approximately 8 inches; fully opened younger leaves (approximately one month of age) approximately 2⅞ inches.

*Width.*—Mature leaves (older than one year of age) approximately 4⅝ inches; fully opened younger leaves (approximately one month of age) approximately 1½ inches.

*Leaf shape.*—Mature leaves (older than one year of age) are substantially obovate in shape, but some younger leaves may have an oval or elliptic shape (as seen in FIG. 4).

*Tip shape.*—Substantially acute to mucronate in all ages.

*Base shape.*—Leaves of all ages may have a very subtly oblique leaf base.

*Margin.*—Margins of mature leaves (older than one year of age) may be substantially entire, occasionally exhibiting mildly undulate margins; margins of younger leaves substantially entire.

*Color of mature leaves, top surface.*—Dark green to medium green (approximately Pantone 574 PC to Pantone 370 PC).

*Color of young leaves, bottom surface.*—Light green (approximately Pantone 7489 PC to 7488 PC).

*Venation pattern.*—Pinnate (substantially alternately pinnate, although some veins may appear oppositely pinnate).

*Midvein color.*—Greenish yellow (approximately Pantone 389 PC to Pantone DS 296-2 C).

*Petiole.*—Approximately 1 to 1½ inches.

*Petiole color.*—Bright green (approximately Pantone DS 298-1 U to Pantone 376 C).

*Leaf arrangement.*—Alternate.

*Anthocyanin coloration.*—Present.

Flowers:

*Flower type.*—Perfect, A-type.

*Flower color.*—White to creamy off-white (white to approximately Pantone S 22-9 C).

*Bud.*—Approximately 1/12 inch in diameter, borne in clusters.

*Inflorescence.*—Determinate inflorescence, with an average of 3 peduncles per inflorescence (cyme) with approximately 20-25 flowers per peduncle. Peduncles approximately 1/16 inch in length.

*Flower abundance.*—Flowers abundant with approximately 75% of the tree covered in flowers during flowering season.

*Bloom date range.*—Flowering duration is approximately two weeks in early spring (late February to early March).

Figure 6:
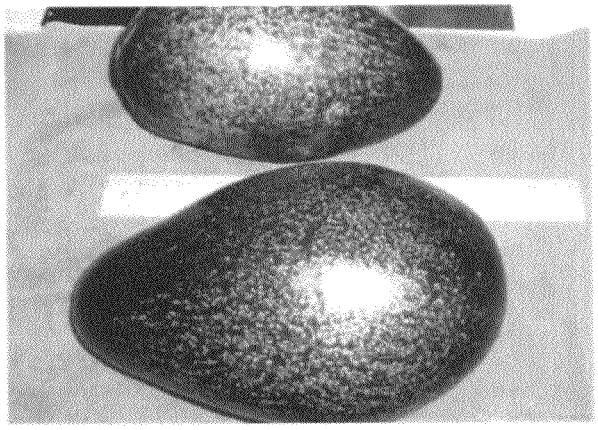
FIGS. 6-8 show ripe 'Pflum's Best' fruit displaying large size and characteristic maroon skin and slightly pebbled to smooth texture.
Figure 7:
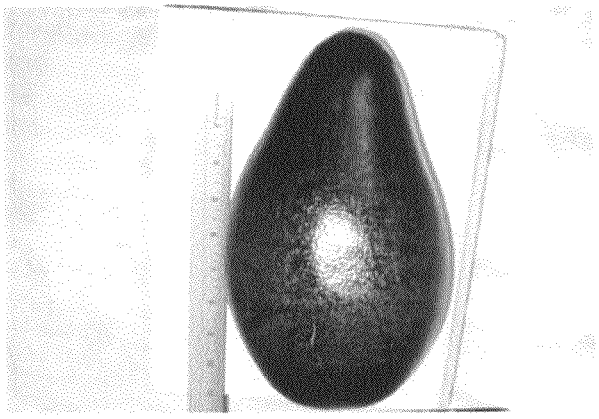
Figure 8:
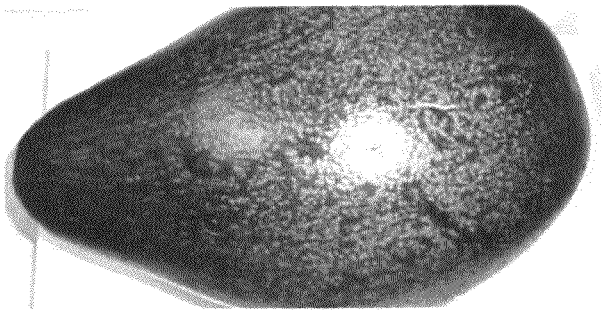

Fruit (as seen in FIGS. 6-8):

*Maturity date range.*—August to September.

*Fruit size.*—Approximately 6-11 inches in length and 4.5 inches in diameter when ripe; approximately 25 ounces.

*Fruit shape.*—Substantially oval, pedicel asymmetrical.

*Skin.*—Ripe color is maroon to brown (including approximately Pantone 1815 M, Pantone 498 PC, and Pantone DS 68-1 C), texture is slightly pebbled to smooth.

*Flesh.*—Buttery yellow color (approximately Pantone 586 UP to Pantone 382 UP) with some darker green (approximately Pantone DS 304-4 U) veins near the outer portion of fruit flesh (near inner surface of skin), texture when ripe is smooth and buttery.

*Seed.*—Approximately 1¾ inches in diameter, located in center of fruit and covered with thin brown skin.

*Eating quality.*—Excellent, fruit has a buttery or nutty flavor.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A new and distinct avocado tree substantially as described and illustrated herein.

* * * * *